United States Patent
West et al.

(10) Patent No.: US 7,279,176 B1
(45) Date of Patent: *Oct. 9, 2007

(54) NITRIC OXIDE-PRODUCING HYDROGEL MATERIALS

(75) Inventors: Jennifer L. West, Houston, TX (US); Kristyn Simcha Bohl, Houston, TX (US)

(73) Assignee: Rice University, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/653,406

(22) Filed: Sep. 1, 2000

Related U.S. Application Data

(60) Provisional application No. 60/152,054, filed on Sep. 2, 1999.

(51) Int. Cl.
*A61F 2/00* (2006.01)
*A61K 9/14* (2006.01)

(52) U.S. Cl. .................................. 424/426; 424/486

(58) Field of Classification Search ............... 424/422, 424/423, 484, 486, 487, 78.08, 78.12, 78.17, 424/78.26, 78.27, 426
See application file for complete search history.

(56) References Cited

U.S. PATENT DOCUMENTS

| | | | |
|---|---|---|---|
| 4,526,938 | A | 7/1985 | Churchill et al. |
| 4,716,203 | A | 12/1987 | Casey et al. |
| 4,741,337 | A | 5/1988 | Smith et al. |
| 4,957,744 | A | 9/1990 | della Valle et al. |
| 4,987,744 | A | 1/1991 | Handley et al. |
| 5,410,016 | A | 4/1995 | Hubbell et al. |

(Continued)

FOREIGN PATENT DOCUMENTS

WO    WO96/15797    5/1996

(Continued)

OTHER PUBLICATIONS

Diodati et al., ."Complexes of Nitric Oxide with Nucleophiles as Agents for the Controlled Biological Release of Nitric Oxide: Hemodynamic Effect in the Rabbit," in Journal of Cardiovascular Pharmacology, 22:287-292.*

(Continued)

*Primary Examiner*—Michael G. Hartley
*Assistant Examiner*—Blessing Fubara
(74) *Attorney, Agent, or Firm*—Kilpatrick Stockton LLP

(57) ABSTRACT

Hydrogels releasing or producing NO, most preferably photopolymerizable biodegradable hydrogels capable of releasing physiological amounts of NO for prolonged periods of time, are applied to sites on or in a patient in need of treatment thereof for disorders such as restenosis, thrombosis, asthma, wound healing, arthritis, penile erectile dysfunction or other conditions where NO plays a significant role. The hydrogels are typically formed of macromers, which preferably include biodegradable regions, and have bound thereto groups that are released in situ to elevate or otherwise modulate NO levels at the site where treatment is needed. The macromers can form a homo or hetero-dispersion or solution, which is polymerized to form a hydrogel material, that in the latter case can be a semi-interpenetrating network or interpenetrating network. Compounds to be released can be physically entrapped, covalently or ionically bound to macromer, or actually form a part of the polymeric material. The hydrogel can be formed by ionic and/or covalent crosslinking. Other active agents, including therapeutic, prophylactic, or diagnostic agents, can also be included within the polymeric material.

18 Claims, 11 Drawing Sheets

1. Synthesis of copolymer

2. Formation of S-nitrosocysteine

3. Photopolymerization

4. Release of NO

U.S. PATENT DOCUMENTS

| | | | |
|---|---|---|---|
| 5,508,317 A | | 4/1996 | Müller |
| 5,632,981 A | * | 5/1997 | Saavedra et al. ......... 424/78.08 |
| 5,665,840 A | | 9/1997 | Pöhlmann et al. |
| 5,807,927 A | | 9/1998 | Stockinger et al. |
| 5,849,839 A | * | 12/1998 | Hubbell et al. ............ 525/54.1 |
| 5,849,841 A | | 12/1998 | Mühlebach et al. |
| 5,879,713 A | * | 3/1999 | Roth et al. ................... 424/489 |
| 5,900,433 A | * | 5/1999 | Igo et al. ..................... 514/530 |
| 5,910,316 A | | 6/1999 | Keefer et al. |
| 5,932,674 A | | 8/1999 | Müller |
| 5,939,489 A | | 8/1999 | Müller |
| 5,994,444 A | * | 11/1999 | Trescony et al. ........... 524/429 |
| 6,011,077 A | | 1/2000 | Müller |
| 6,262,206 B1 | * | 7/2001 | Nesvadba et al. .......... 526/220 |
| 6,299,604 B1 | * | 10/2001 | Ragheb et al. .............. 604/265 |

FOREIGN PATENT DOCUMENTS

| | | |
|---|---|---|
| WO | WO96/32136 | * 10/1996 |
| WO | WO 96/32136 | 10/1996 |
| WO | WO 01/15738 | 3/2001 |

OTHER PUBLICATIONS

Lin et al. ("Nitric Oxide-based molecular strategies for restenosis therapy" in Expert Opinion on Therapeutic Patents, 15:483-495 (2005)),.*

D.J. Smith et al., "Nitric Oxide-Releasing Polymers Containing the 'N(O)NO!- Group", Journal of Medicinal Chemistry, vol. 39, (1996) pp. 1148-1156.

Bohl, K. et al., "Nitric oxide-producing materials: a potential therapy for thrombosis and restenosis", Proc. Int. Symp. Controlled Release Bioact. Mater., (1999) 26th, pp. 56-57.

Bohl, K. et al., "Niric oxide-releasing materials for the prevention of thrombosis and restenosis", Proc. Int. Symp. Controlled Release Bioact. Mater., (2000), 27th, pp. 143-144.

Bohl, K.S. et al., "Nitric oxide-generating polymers reduce platelet adhesion and smooth muscle cell proliferation", Biomaterials, (2000), 21(22), pp. 2273-2278.

DATABASE WPI, Derwent Publications, Ltd., London, GB, Section Ch, Week 200061, Class B05, AN 2000-630208.

Bohl et al., "Nitric oxide-generating polymers reduce platelet adhesion and smooth muscle cell proliferation", Biomaterials, 2000, 2273-2278, vol. 21.

Bohl et al., "Nitric Oxide-Releasing Materials for the Prevention of Thrombosis and Restenosis", Proceed. Int'l. Sym. Control. Rel. Bioact. Mater., 2000, 143-144, vol. 27.

Bohl et al., "Nitric Oxide Producing Materials: A Potential Therapy for Thrombosis Restenosis", Proceed. Int'l. Sym. Control. Rel. Bioact. Mater., 1999, 56-57, vol. 26.

Bohl et al., "Nitric Oxide-Releasing Hydrogels for the Prevention of Thrombosis and Restenosis", Circulation, Oct. 31, 2000; II.734, vol. 102, No. 18 (Abstract only).

Cohn et al, "Biodegradable PEO/PLA block polymers", J. Biomed. Mater. Res., 1988, 993-1009, vol. 22.

Cooke et al., "Antiatherogenic Effects of L-Arginine in the Hypercholesterolemic Rabbit", J. Clin. Invest., 1992, 1168-1172, vol. 90.

De Graaf et al., "Nitric Oxide Functions as an Inhibitor of Platelet Adhesion Under Flow Conditions", Circulation, 1992, 2284-2290, vol. 85.

De Meyer et al., "Effect of Nitric Oxide Donors on Neointima Formation and Vascular Reactivity in the Collared Carolid Artery of Rabbits", J. Cardiovasc. Res., 1995, 272-279, vol. 26.

Diodati et al., "Complexes of Nitric Oxide with Nucleophiles as Agents for the Controlled Biological Release of Nitric Oxide: Hemodynamic Effect in the Rabbit", J. Cardiovasc. Pharm., 1993, 287-292, vol. 22.

Diodati et al., "Complexes of Nitric Oxide with Nucleophiles as Agents for the Controlled Biological Release of Nitric Oxide: Antiplatelet Effect", Throm. Haem., 1993, 654-658, 1993.

Garg et al., "Nitric Oxide-Generating Vasodilators and 8-Bromo Cyclic Guanosine Monophosphate Inhibit Mitogenesis and Proliferation of Cultured Rat Vascular Smooth Muscle Cells", J. Clin. Invest., 1989, 1774-1777, vol. 83.

Greenhalgh, "The Role of Growth Factors in Wound Healing", J. Trauma, 1996, 159-167, vol. 41.

Heller et al., "Nitric Oxide Inhibits Proliferation of Human Endothelial Cells via a Mechanism Independent of cGMP". Atherosclerosis, 1999, 49-57, vol. 144.

Hern et al., "Incorporation of Adhesion Peptides into Nonadhesive Hydrogels Useful for Tissue Resurfacing", J. Biomed. Mater. Res., 1998, 266-276, vol. 39.

Holland et al., Polymers for Biodegradable Medical Devices. 1. The Potential of Polyesters as Controlled Macromolecular Release Systems, 1986, 155-180, vol. 4.

Ignarro et al., "Mechanism of Vascular Smooth Muscle Relaxation by Organic Nitrates, Nitrites, Nitroprusside and Nitric Oxide: Evidence for the Involvement of S-Nitrosothiols as Active Intermediates", J. Pharmacol. Exp. Ther., 1981, 739-749, vol. 218.

Kwon et al., "Inhibition of Tumor Cell Ribonucleotide Reductase by Macrophage-derived Nitric Oxide", J. Exp. Med., 1991, 761-767, vol. 174.

Lefer et al., "Antineutrophil and Myocardial Protecting Actions of a Novel Nitric Oxide Donor After Acute Myocardial Ischemia and Reperfusion in Dogs", Circulation, 1993, 2337-2350, vol. 88.

Legrand et al., "Preclinical Promise of Becaplermin (rhPDGF-BB) in Wound Healing", Am. J. Surg., 1998, 48S-54S, vol. 176.

Lepoivre et al., "Inactivation of Ribonucleotide Reductase by Nitric Oxide", Biochem. Biophys. Res. Comm., 1991, 442-448, vol. 179.

Mann et al., "Tethered-TGF-β Increases Extracellular Matrix Production of Vascular Smooth Muscle Cells", Biomaterials, 2001, 439-444, vol. 22.

Maragos et al., "Nitric Oxide/Nucleophile Complexes Inhibit the in Vitro Proliferation of A375 Melanoma Cells via Nitric Oxide Release", Cancer Res., 1993, 564-568, vol. 53.

Martinez-De Jesus et al., "Randomized Single-Blind Trial of Topical Ketanserin for Healing Acceleration of Diabetic Foot Ulcers", Arch. Med. Res., 1997, 95-99, vol. Spring 28 (1) (Abstract only).

Mathews et al., "Biological Activity of S-Nitrosothiols: The Role of Nitric Oxide", J. Pharmacol. Exp. Therap., 1993, 1529-1537, vol. 267.

Moro et al., "cGMP Mediates the Vascular and Platelet Actions of Nitric Oxide: Confirmation Using an Inhibitor of the Soluble Guanylyl Cyclase", Proc. Natl. Acad. Sci. USA, 1996, 1480-1485, vol. 93.

Rodomski et al., "Comparative Pharmacology of Endothelium-Derived Relaxing Factor, Nitric Oxide and Prostacyclin in Platelets", Br. J. Pharmacol., 1987, 181-187, vol. 92.

Sarkar et al., "Nitric Oxide Inhibition of Endothelial Cell Mitogenesis and Proliferation", Surgery, 1995, 274-279, vol. 118.

Sawhney et al., "Rapidly Degraded Terpolymers of dl-Lactide, Glycolide, and ε-Caprolactone with Increased Hydrophilicity by Copolymerization with Polyethers", J. Biomed. Res., 1990, 1397-1411, vol. 24.

Scott-Burden et al., "Extracellular Matrix: Differential Influence on Growth and Biosynthesis Patterns of Vascular Smooth Muscle Cells from SHR and WKY Rats", J. Cell Physiol., 1989, 267-274, vol. 141.

Scott-Burden et al., "Genetically Engineered Smooth Muscle Cells as Linings to Improve the Biocompatibility of Cardiovascular Prostheses", Circulation, 1996, II235-238, vol. 94 (9 Suppl.).

Smith et al., "Nitric Oxide-Releasing Polymers Containing the [N(O)NO] Group", J. Med. Chem., 1996, 1148-1156, vol. 39.

Spilizewski et al., "The Effect of Hydrocortisone Acetate Loaded Poly (DL-Lactide) Films on the Inflammatory Response", J. Control. Rel., 1985, 197-203, vol. 2.

Stuehr et al., "Nitric Oxide—A Macrophage Product Responsible for Cytostasis and Respiratory Inhibition in Tumor Target Cells", J. Exp. Med., 1989, 1543-1555, vol. 169.

Williams et al., "Safety and Tolerability of Intravenous-to-Oral Treatment and Single-Dose Intravenous or Oral Prophylaxis with Trovafloxacin". Am. J. Surg., 1998, 74S-79S. vol. 176.

Wieman et al., "Efficacy and Safety of a Topical Gel Formulation of Recombinant Human Platelet-Derived Growth Factor-BB (Becaplermin) in Patients with Chronic Neuropathic Diabetic Ulcers", Diabetes Care, 1998, 822-827, vol. 21.

Ziche et al., "Nitric Oxide Promotes DNA Synthesis and Cyclic GMP Formation in Endothelial Cells from Postcapillary Venules", Biochem. Biophys. Res. Comm., 1993, 1198-1203, vol. 192.

Abstract, Derwent WPI, HU 9801673 A1 (Aug. 28, 2000), (Cycl-N) Cyclolab Ciklodextrin Kutato Fejleszto.

* cited by examiner

1. Synthesis of copolymer

2. Formation of NO - nucleophile complex

ACRL-PEG-DETA + NO gas in $H_2O$ ⟶ ACRL-PEG-DETA-[N(O)NO]⁻

3. Photopolymerization

4. Release of NO

NITRIC OXIDE-PRODUCING HYDROGEL MATERIALS

FIELD OF THE INVENTION

The present invention relates to polymerizable hydrogel materials that produce physiologically relevant amounts of nitric oxide (NO) for prolonged periods of time.

This application claims priority to U.S. Ser. No. 60/152,054 filed Sep. 2, 1999.

BACKGROUND OF THE INVENTION

Endothelial cells, normally present as a monolayer in the intimal layer of the arterial wall, are believed to play an important role in the regulation of smooth muscle cell (SMC) proliferation in vivo. Endothelial cells are seriously disrupted by most forms of vascular injury, including that caused by percutaneous transluminal coronary angioplasty and similar procedures. Approximately 35-50% of patients treated by percutaneous transluminal coronary angioplasty experience clinically significant renarrowing of the artery, or restenosis, within six months of the initial treatment. Restenosis is due, at least in part, to migration and proliferation of smooth muscle cells in the arterial wall along with increases in secretion of matrix proteins to form an obstructive neointimal layer within the arterial wall. Similar issues limit the performance of vascular grafts. The processes that regulate arterial wound healing following vascular injury, such as that caused by angioplasty, are as yet poorly understood, but are believed to involve a complex cascade of blood and vessel wall-derived factors.

Numerous factors that stimulate intimal thickening and restenosis have been identified through administration of exogenous proteins, genetic alteration of cells, or through the blockade of certain signals using antibodies or other specific growth factor inhibitors. These smooth muscle cell mitogens and chemoattractants derive from both the blood or thrombus formation and from the vessel wall itself. Endothelial cells produce a number of substances known to down-regulate smooth muscle cell proliferation, including heparin sulfate, prostacyclin (PG12), and NO.

NO is an endothelium-derived target molecule useful for the prevention of restenosis because, in addition to limiting the proliferation of smooth muscle cells (Garg et al. (1989) *J. Clin. Invest.* 83:1774-7), NO reduces platelet aggregation (de Graaf et al., (1992) *Circulation* 85:2284-90; Radomski et al., (1987) *Br. J. Pharmacol.* 92:181-7), increases endothelial cell proliferation (Ziche et al.,(1993) *Biochem. Biophys. Res. Comm.* 192:1198-1203), and attenuates leukocyte adhesion (Lefer et al., (1993) *Circulation* 88:2337-50), all of which are highly desirable for the reduction of intimal thickening and restenosis (Loscalzo, (1996) *Clin. Appl. Thromb. Hemostas.* 2:7-10). Because of the complexity of the restenotic process, approaches that act upon multiple targets are the most likely to be successful.

The mechanisms whereby NO affects these multiple responses are not fully understood as yet, but it is known that NO activates soluble guanylate cyclase by binding to its heme moiety, thereby elevating the levels of cyclic guanosine monophosphate (cGMP), an intracellular second messenger with multiple cellular effects (Moro et al., (1996) *Proc. Natl. Acad. Sci. USA* 93:1480-5). The effects of NO can often be mimicked by the administration of cGMP or more stable derivatives of cGMP (Garg et al., (1989) *J. Clin. Invest.* 83:1774-7). In addition, NO has been found to inhibit ribonucleotide reductase, an enzyme that converts ribonucleotides into deoxy ribonucleotides, thus significantly impacting DNA synthesis (Lepoivre et al., (1991) *Biochem. Biophys. Res. Comm.* 179:442-8; Kwon et al., (1991) *J. Exp. Med.* 174:761-7), as well as several enzymes involved in cellular respiration (Stuehr et al., (1989) *J. Exp. Med.* 169:1543-55).

A number of molecules that produce NO under physiological conditions (NO donors) have been identified and evaluated both in vitro and in vivo. NO donor molecules exert biological effects mimicking those of NO and include S-nitrosothiols (Diodati et al, (1993) *Thromb. Haem.* 70:654-8; Lefer et al., (1993) *Circulation* 88:2337-50; DeMeyer et al., (1995) *J. Cardiovasc. Pharmacol.* 26:272-9), organic nitrates (Ignarro et al., (1981) *J. Pharmacol. Exp. Ther.* 218:739-49), and complexes of NO with nucleophiles (Diodati et al., (1993) *Thromb. Haem.* 70:654-8; Diodati et al. (1993) *J. Cardiovasc. Pharmacol.* 22:287-92; Maragos et al., (1993) *Cancer Res.* 53:564-8). Most of these have been low molecular weight molecules that are administered systemically and have short half-lives under physiologic conditions, thus exerting effects upon numerous tissue types with a brief period of activity. In addition, L-arginine is often thought of as a NO donor, as L-arginine is a substrate for NO synthase, and thus administration of L-arginine increases endogenous NO production and elicits responses similar to those caused by NO donors in most cases (Cooke et al., (1992) *J. Clin. Invest.* 90:1168-72).

The development of NO-releasing polymers containing NO/nucleophile complexes has been reported by Smith et al., (1996) *J. Med. Chem.* 39:1148-56). These materials were capable of releasing NO for as long as 5 weeks in vitro and were able to limit smooth muscle cell proliferation in culture and to reduce platelet adherence to vascular graft materials in an arterio-venous shunt model. These materials show promise for numerous clinical applications where localized NO production would be desired, such as anti-thrombotic coating materials for catheters, but probably will not be useful for the direct treatment of tissues in vivo as these materials suffer from a number of disadvantages. These polymers may be produced as films, powders, or microspheres, but they cannot be formed in situ in direct contact with cells and tissues, thus making it difficult to strictly localize NO treatment to a tissue and potentially causing issues with the retention of the polymer at the site of application. The formulation issues will also make local administration during laparoscopic or catheter-based procedures difficult or impossible. Additionally, biocompatibility of the base polymer is a serious issue for implantable, NO-releasing polymers, especially those intended for long-term use, as inflammatory and thrombotic responses may develop after the cessation of NO release.

It would be more efficient if these compounds could be administered solely to the site in need of treatment, and in some cases, reduce or eliminate side effects due to systemic administration of the agents, particularly over prolonged time periods.

It is therefore an object of the present invention to provide reagents for controlled release of NO and/or compounds modulating NO levels at a particular site, following local or topical application.

It is a further object of the present invention to provide methods for treatment of conditions involving inflammatory responses by providing hydrogel materials releasing compounds modulating NO levels at the site of application.

SUMMARY OF THE INVENTION

Biocompatible polymeric materials releasing or producing physiological amounts of NO for prolonged periods of time, are applied to sites on or in a patient in need of treatment thereof for disorders such as restenosis, thrombosis, asthma, wound healing, arthritis, penile erectile dysfunction or other conditions where NO plays a significant role. The polymeric materials can also be formed into films, coatings, or microparticles. The polymers are typically formed of macromers, which may include biodegradable regions, and have bound thereto groups that are released in situ to elevate or otherwise modulate levels at the site where treatment is needed. The macromers can form a homo or hetero-dispersion or solution, which is polymerized to form a polymeric material, that in the latter case can be a semi-interpenetrating network or interpenetrating network. Compounds to be released can be physically entrapped, covalently or ionically bound to macromer, or actually form a part of the polymeric material. Hydrogels can be formed by ionic and/or covalent crosslinking. Other active agents, including therapeutic, prophylactic, or diagnostic agents, can also be included within the polymeric material.

BRIEF DESCRIPTION OF THE DRAWINGS

FIG. 8A, % of control cell number, hydrogel formulation. FIG. 8B, % of control cell number, soluble polymer.

DETAILED DESCRIPTION OF THE INVENTION

Figure 1:
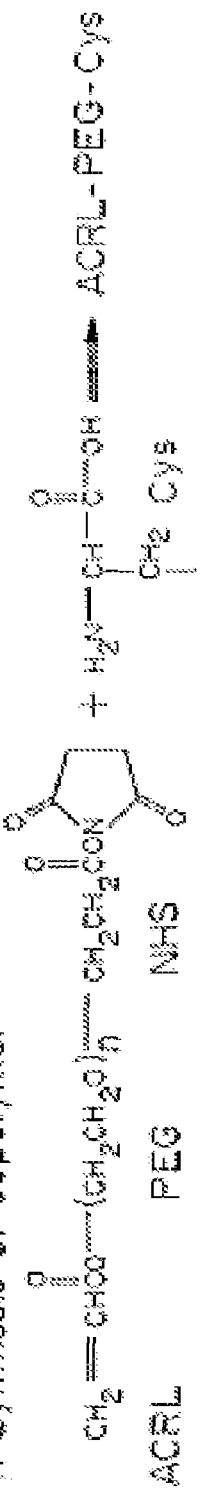
FIG. 1 is a schematic of the synthesis of S-nitrosocysteine hydrogels (Acryloyl-PEG-Cys-NO).
Figure 1:
Figure 1:
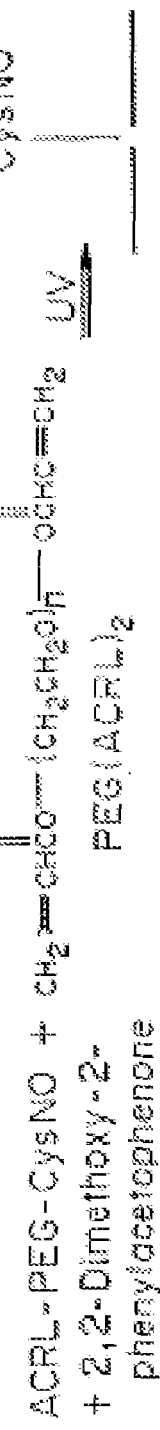
Figure 1:

I. Polymeric Materials for Release of NO

The polymeric materials are biocompatible and release or produce NO. In various preferred embodiments, the polymers are also biodegradable, form hydrogels, polymerize in situ and are tissue adherent. These properties are conferred by the selection of the macromer components as well as addition of various groups to the components.

The term "polymerizable" means that the regions have the capacity to form additional covalent bonds resulting in macromer interlinking, for example, carbon-carbon double bond of acrylate-type molecules. Such polymerization is characteristically initiated by free-radical formation resulting from photon absorption of certain dyes and chemical compounds to ultimately produce free-radicals, although it can be obtained using other methods and reagents known to those skilled in the art.

A. Polymeric Materials

The polymeric materials must be biocompatible, i.e., not eliciting a significant or unacceptable toxic or immunogenic response following administration to or implantation into an individual.

A number of polymeric materials are known which are biocompatible, including both natural and synthetic polymers. Examples include proteins (of the same origin as the recipient), polysaccharides such as chondroitin sulfate and hyaluronic acid, polyurethanes, polyesters, polyamides, and acrylates. Polymers can be degradable or non-degradable.

Most polymeric materials will be selected based on a combination of properties conferred by the various components, which may include water soluble regions such as PEG or PVA, biodegradable regions such as regions that degrade hydrolytically, and groups that can be used to polymerize the macromers in situ.

Water-Soluble and/or Tissue Adhesive Regions

There are a variety of water soluble materials that can be incorporated into the polymers. The term "at least substantially water soluble" is indicative that the solubility should be at least about 5 g/100 ml of aqueous solution. In preferred embodiments, the core water soluble region can consist of poly(ethylene glycol), poly(ethylene oxide), poly(vinyl acetate), poly(vinyl alcohol), poly(vinylpyrrolidone), poly (ethyloxazoline), poly(ethylene oxide)-co-poly(propyleneoxide) block copolymers, polysaccharides or carbohydrates such as hyaluronic acid, dextran, heparin sulfate, chondroitin sulfate, heparin, or alginate, or proteins such as gelatin, collagen, albumin, or ovalbumin.

Hydrophilic (i.e., water soluble) regions will generally be tissue adhesive. Both hydrophobic and hydrophilic polymers which include a large number of exposed carboxylic groups will be tissue adhesive or bioadhesive. Ligands such as RGD peptides and lectins which bind to carbohydrate molecules on cells can also be bound to the polymer to increase tissue adhesiveness.

Degradable Regions

Polyesters (Holland et al., 1986 *Controlled Release*, 4:155-180) of α-hydroxy acids (viz., lactic acid, glycolic acid), are the most widely used biodegradable materials for applications ranging from closure devices (sutures and staples) to drug delivery systems (U.S. Pat. No. 4,741,337 to Smith et al.; Spilizewski et al., 1985 *J. Control. Rel.* 2:197-203). In addition to the poly(hydroxy acids), several other polymers are known to biodegrade, including polyanhydrides and polyorthoesters, which take advantage of labile backbone linkages, as reported by Domb et al., 1989 *Macromolecules,* 22:3200; Heller et al., 1990 *Biodegradable Polymers as Drug Delivery Systems,* Chasin, M. and Langer, R., Eds., Dekker, New York, 121-161. Polyaminoacids have also been synthesized since it is desirable to have polymers that degrade into naturally occurring materials, as reported by Miyake et al., 1974, for in vivo use.

The time required for a polymer to degrade can be tailored by selecting appropriate monomers. Differences in crystallinity also alter degradation rates. Due to the relatively hydrophobic nature of these polymers, actual mass loss only begins when the oligomeric fragments are small enough to be water soluble. Hence, initial polymer molecular weight influences the degradation rate.

The biodegradable region is preferably hydrolyzable under in vivo conditions. Hydrolyzable groups may be polymers and oligomers of glycolide, lactide, $\epsilon$-caprolactone, other $\alpha$-hydroxy acids, and other biologically degradable polymers that yield materials that are non-toxic or present as normal metabolites in the body. Preferred poly ($\alpha$-hydroxy acid)s are poly(glycolic acid), poly(DL-lactic acid) and poly(L-lactic acid). Other useful materials include poly(amino acids), poly(anhydrides), poly(orthoesters), and poly(phosphoesters). Polylactones such as poly($\epsilon$-caprolactone), poly($\epsilon$-caprolactone), poly($\delta$-valerolactone) and poly (gamma-butyrolactone), for example, are also useful.

Biodegradable regions can also be constructed from polymers or monomers using linkages susceptible to biodegradation by enzymes, such as ester, peptide, anhydride, orthoester, and phosphoester bonds. Degradable materials of biological origin are well known, for example, crosslinked gelatin. Hyaluronic acid has been crosslinked and used as a degradable swelling polymer for biomedical applications (U.S. Pat. No. 4,987,744 to della Valle et al., U.S. Pat. No. 4,957,744 to Della Valle et al. (1991) *Polym. Mater. Sci. Eng.,* 62:731-735]).

Biodegradable Hydrogels

A number of polymers have been described which include both water soluble regions and biodegradable regions. Sawhney et al., (1990) *J. Biomed. Mater. Res.* 24:1397-1411, copolymerized lactide, glycolide and $\epsilon$-caprolactone with PEG to increase its hydrophilicity and degradation rate. U.S. Pat. No. 4,716,203 to Casey et al. (1987) synthesized a PGA-PEG-PGA block copolymer, with PEG content ranging from 5-25% by mass. U.S. Pat. No. 4,716,203 to Casey et al. (1987) also reports synthesis of PGA-PEG diblock copolymers, again with PEG ranging from 5-25%. U.S. Pat. No. 4,526,938 to Churchill et al. (1985) described non-crosslinked materials with MW in excess of 5,000, based on similar compositions with PEG; although these materials are not water soluble. Cohn et al. (1988) *J. Biomed. Mater. Res.* 22:993-1009 described PLA-PEG copolymers that swell in water up to 60%; these polymers also are not soluble in water, and are not crosslinked. The features that are common to these materials are that they use both water-soluble polymers and degradable polymers, and that they are insoluble in water, collectively swelling up to about 60%.

U.S. Pat. No. 5,410,016 issued on Apr. 25, 1995 to Hubbell, et al., describes materials which are based on polyethylene glycol (PEG), because of its high biocompatible and thromboresistant nature, with short polylactide extensions to impart biodegradation and acrylate termini to allow rapid photopolymerization without observable heat production. These materials are readily modified to produce hydrogels which release or produce NO.

The polymerizable regions are separated by at least one degradable region to facilitate uniform degradation in vivo. There are several variations of these polymers. For example, the polymerizable regions can be attached directly to degradable extensions or indirectly via water soluble nondegradable sections so long as the polymerizable regions are separated by a degradable section. For example, if the macromer composition contains a simple water soluble region coupled to a degradable region, one polymerizable region may be attached to the water soluble region and the other attached to the degradable extension or region. In another embodiment, the water soluble region forms the central core of the macromer composition and has at least two degradable regions attached to the core. At least two polymerizable regions are attached to the degradable regions so that, upon degradation, the polymerizable regions, particularly in the polymerized gel form, are separated. Conversely, if the central core of the macromer composition is formed by a degradable region, at least two water soluble regions can be attached to the core and polymerizable regions can be attached to each water soluble region. The net result will be the same after gel formation and exposure to in vivo degradation conditions.

In another embodiment, the macromer composition has a water soluble backbone region and a degradable region affixed to the macromer backbone. At least two polymerizable regions are attached to the degradable regions, so that they are separated upon degradation, resulting in gel product dissolution. In a further embodiment, the macromer backbone is formed of a nondegradable backbone having water soluble regions as branches or grafts attached to the degradable backbone. Two or more polymerizable regions are attached to the water soluble branches or grafts. In another variation, the backbone may be star shaped, which may include a water soluble region, a biodegradable region or a water soluble region which is also biodegradable. In this general embodiment, the star region contains either water soluble or biodegradable branches or grafts with polymerizable regions attached thereto. Again, the polymerizable regions must be separated at some point by a degradable region.

Polymerizable Groups

The polymerizable regions may be polymerizable by photoinitiation by free radical generation, most preferably in the visible or long wavelength ultraviolet radiation. The preferred polymerizable regions are acrylates, diacrylates, oligoacrylates, dimethacrylates, oligomethoacrylates, or other biologically acceptable photopolymerizable groups. A preferred tertiary amine is triethanol amine.

Useful photoinitiators are those which can be used to initiate by free radical generation polymerization of the macromers without cytotoxicity and within a short time frame, minutes at most and most preferably seconds. Preferred dyes as initiators of choice for LWUV initiation are ethyl eosin, 2,2-dimethoxy-2-phenyl acetophenone, other acetophenone derivatives, and camphorquinone. In all cases, crosslinking and polymerization are initiated among copolymers by a light-activated free-radical polymerization initiator such as 2,2-dimethoxy-2-phenylacetophenone or a combination of ethyl eosin ($10^{-4}$-$10^{-2}$ milliM) and triethanolamine (0.001 to 0.1 M), for example.

The choice of the photoinitiator is largely dependent on the photopolymerizable regions. For example, when the macromer includes at least one carbon-carbon double bond, light absorption by the dye causes the dye to assume a triplet state, the triplet state subsequently reacting with the amine to form a free radical which initiates polymerization. Preferred dyes for use with these materials include eosin dye and initiators such as 2,2-dimethyl-2-phenylacetophenone, 2-methoxy-2-phenylacetophenone, and camphorquinone. Using such initiators, copolymers may be polymerized in situ by long wavelength ultraviolet light or by laser light of about 514 nm, for example.

Initiation of polymerization is accomplished by irradiation with light at a wavelength of between about 200-700 nm, most preferably in the long wavelength ultraviolet range or visible range, 320 nm or higher, most preferably about 514 nm or 365 nm.

There are several photooxidizable and photoreducible dyes that may be used to initiate polymerization. These include acridine dyes, for example, acriblarine; thiazine dyes, for example, thionine; xanthine dyes, for example, rose bengal; and phenazine dyes, for example, methylene blue. These are used with cocatalysts such as amines, for example, triethanolamine; sulphur compounds, for example, $RSO_2R_1$; heterocycles, for example, imidazole; enolates; organometallics; and other compounds, such as N-phenyl glycine. Other initiators include camphorquinones and acetophenone derivatives.

Thermal polymerization initiator systems may also be used. Such systems that are unstable at 37° C. and would initiate free radical polymerization at physiological temperatures include, for example, potassium persulfate, with or without tetramethyl ethylenediamine; benzoylperoxide, with or without triethanolamine; and ammonium persulfate with sodium bisulfite.

Other initiation chemistries may be used besides photoinitiation. These include, for example, water and amine initiation schemes with isocyanate or isothiocyanate containing macromers used as the polymerizable regions.

Preferred Embodiments

In a preferred embodiment, the polymeric materials are a biodegradable, polymerizable and at least substantially water soluble macromer composition. The first macromer includes at least one water soluble region, at least one NO carrying region and at least one free radical-polymerizable region. The second macromer includes at least one water soluble region and at least two free radical polymerizable regions. The regions can, in some embodiments, be both water soluble and biodegradable. The macromer composition is polymerized by exposure of the polymerizable regions to free radicals generated, for example, by photosensitive chemicals and dyes.

Examples of these macromers are PVA or PEG-oligoglycolyl-acrylates. The choice of appropriate end caps permits rapid polymerization and gelation. Acrylates are preferred because they can be polymerized using several initiating systems, e.g., an eosin dye, by brief exposure to ultraviolet or visible light. A poly(ethyleneglycol) or PEG central structural unit (core) is preferred on the basis of its high hydrophilicity and water solubility, accompanied by excellent biocompatibility. A short oligo or poly(α-hydroxy acid), such as polyglycolic acid, is selected as a preferred chain extension because it rapidly degrades by hydrolysis of the ester linkage into glycolic acid, a harmless metabolite. Although highly crystalline polyglycolic acid is insoluble in water and most common organic solvents, the entire macromer composition is water-soluble and can be rapidly gelled into a biodegradable network while in contact with aqueous tissue fluids. Such networks can be used to entrap and homogeneously disperse water-soluble drugs and enzymes and to deliver them at a controlled rate. Further, they may be used to entrap particulate suspensions of water-insoluble drugs. Other preferred chain extensions are polylactic acid, polycaprolactone, polyorthoesters, and polyanhydrides. Polypeptides may also be used. Such "polymeric" blocks should be understood to include timeric, dimeric, and oligomeric blocks.

PVA contains many pendant hydroxyl groups. These hydroxyl groups are easily reacted to form side chains such as various crosslinking agents and nitric oxide donors. PVA is water soluble and has excellent biocompatibility. Modification of PVA to attach methacrylate groups via a diacetal bond with the pendant hydroxyl groups and addition of an appropriate photoinitiator enables the PVA to be photopolymerized to form hydrogels under long wavelength UV light. In another preferred embodiment, the hydrogel is formed from modified polyvinyl alcohol (PVA) macromers, such as those described in U.S. Pat. Nos. 5,508,317, 5,665,840, 5,849,841, 5,932,674, 6,011,077, 5,939,489, and 5,807,927. The macromers disclosed in U.S. Pat. No. 5,508,317, for example, are PVA prepolymers modified with pendant crosslinkable groups, such as acrylamide groups containing crosslinkable olefinically unsaturated groups. These macromers can be polymerized by photopolymerization or redox free radical polymerization, for example. The starting polymers are, in particular, derivatives of polyvinyl alcohol or copolymers of vinyl alcohol that contain, for example, a 1,3-diol skeleton. The crosslinkable group or the further modifier can be bonded to the starting polymer skeleton in various ways, for example through a certain percentage of the 1,3-diol units being modified to give a 1,3-dioxane, which contains a crosslinkable radical, or a further modifier in the 2-position. Another possibility is for a certain percentage of hydroxyl groups in the starting polymer to be esterified by means of an unsaturated organic acid, these ester-bonded radicals containing a crosslinkable group. The hydrophobicity of these macromers can be increased by substituting some of the pendant hydroxyl groups with more hydrophobic substituents. The properties of the macromers, such as hydrophobicity, can also be modified by incorporating a comonomer in the macromer backbone. The macromers can also be formed having pendant groups crosslinkable by other means.

B. NO groups or Modulating Compounds

A number of molecules that produce NO under physiological conditions (NO donors) have been identified and evaluated both in vitro and in vivo, including S-nitrosothiols, organic nitrates, and complexes of NO with nucleophiles. L-arginine is a NO donor, since L-arginine is a substrate for NO synthase, and thus administration of L-arginine increases endogenous NO production and elicits responses similar to those caused by NO donors in most cases. Other NO donors include molsidomine, CAS754, SPM-5185, and SIN-1. Other compounds capable of producing and/or donating NO may also be used. These include organic nitrates, nitrosylating compounds, nitrosoesters, and L-arginine.

The molecules which produce NO, or release or generate NO, are preferably attached to regions containing nucleophiles and/or thiols such as S-nitrosothiols capable of forming a complex with NO.

C. Prophylactic, Therapeutic and Diagnostic Agents

The polymeric materials can also be used for drug delivery, preferably localized release of prophylactic, therapeutic or diagnostic agents at the site where the materials are needed, although the polymeric materials can be loaded with agent to be released systemically. These agents include proteins or peptides, polysaccharides, nucleic acid molecules, and simple organic molecules, both natural and synthetic. Representative materials include antibiotics, antivirals, and antifungal drugs, anti-inflammatories (steroidal or non-steroidal), hormones, growth factors, cytokines, neuroactive agents, vasoconstrictors and other molecules involved in the cardiovascular responses, enzymes, antineoplastic agents, local anesthetics, antiangiogenic agents, antibodies, drugs affecting reproductive organs, and oligonucleotides such as antisense oligonucleotides. Diagnostic materials may be radioactive, bound to or cleave a chromogenic substrate, or detectable by ultrasound, x-ray, MRI, or other standard imaging means.

These agents can be mixed with macromer prior to polymerization, applied into or onto the polymer, or bound to the macromer prior to or at the time of polymerization, either covalently or ionically, so that the agent is released by degradation (enzymatic or hydrolytic) or diffusion at the site where the polymer is applied.

II. Method of Use

A. Coatings; Films; Microparticles

Although described primarily with respect to in vivo treatment, it is apparent that the polymeric materials described herein can be used in cell culture, on cell culture substrates, or as coatings on medical implants or devices such as stents or catheters, or formed using standard techniques into microparticles or other types of formulations which may be used in or administered to a patient.

B. Therapeutic Applications

Polymeric materials capable of releasing physiological amounts of NO for prolonged periods of time can be applied to sites on or in a patient in need of treatment thereof. Representative disorders or conditions that can be treated with NO include restenosis, thrombosis, asthma, would healing, arthritis, and penile or female erectile dysfunction. The material is typically applied as a macromer solution and polymerized in situ, although polymerization can be initiated prior to application.

Wound Healing

The formulations are particularly useful for treatment of all types of wounds, including burns, surgical wounds, and open leg and foot wounds. There are generally three types of open leg wounds, termed ulcers: venous stasis ulcers, generally seen in sedentary elderly people when blood flow to the leg becomes sluggish; decubitus ulcers, also termed pressure sores or bed sores, which occurs most often in people who are bedridden and are unable to frequently change position; and diabetic foot ulcers, caused by poor blood circulation to the feet. Due to the aging of the population, there will likely be a greater demand for effective and user friendly wound treatments in the near future.

The term "wound" as used herein refers to all types of tissue injuries, including those inflicted by surgery and trauma, including burns, as well as injuries from chronic or acute medical conditions, such as atherosclerosis or diabetes.

Treatment of Restenosis

A preferred application is a method of reducing the effects of restenosis on post-surgical patients. The method includes coating the surface within an artery with an aqueous solution of light-sensitive free radical polymerizable initiator and a number of macromers. The coated artery is subjected to a Xenon arc laser inducing polymerization of the macromers. As the newly polymerized macromer composition is formed, the physiological conditions within the artery will induce the release of NO. This release will be strictly localized for prolonged periods of time.

Prevention of Surgical Adhesions

A preferred application is a method of reducing formation of adhesions after a surgical procedure in a patient. In one embodiment the method includes coating damaged tissue surfaces in a patient with an aqueous solution of a light-sensitive free-radical polymerization initiator and a macromer solution as described above. The coated tissue surfaces are exposed to light sufficient to polymerize the macromer. The light-sensitive free-radical polymerization initiator may be a single compound (e.g., 2,2-dimethoxy-2-phenyl acetophenone) or a combination of a dye and a cocatalyst (e.g., ethyl eosin and triethanol amine).

Tissue Adhesives

Another use of the polymers is in a method for adhering tissue surfaces in a patient. In one embodiment the macromer is mixed with a photoinitiator or photoinitiator/cocatalyst mixture to form an aqueous mixture and the mixture is applied to a tissue surface to which tissue adhesion is desired. The tissue surface is contacted with the tissue with which adhesion is desired, forming a tissue junction. The tissue junction is then irradiated until the macromers are polymerized.

Tissue Coatings

In a particularly preferred application of these macromers, an ultrathin coating is applied to the surface of a tissue, most preferably the lumen of a tissue such as a blood vessel. One use of such a coating is in the treatment or prevention of restenosis, abrupt reclosure, or vasospasm after vascular intervention. An initiator is applied to the surface of the tissue, allowed to react, adsorb or bond to tissue, the unbound initiator is removed by dilution or rising, and the macromer solution is applied and polymerized. This method is capable of creating uniform polymeric coating of between one and 500 microns in thickness, most preferably about twenty microns, which does not evoke thrombosis or localized inflammation.

Tissue Supports

The polymeric materials can also be used to create tissue supports by forming shaped articles within the body to serve a mechanical function. Such supports include, for example, sealants for bleeding organs, sealants for bone defects and space-fillers for vascular aneurisms. Further, such supports can include strictures to hold organs, vessels or tubes in a particular position for a controlled period of time.

Controlled Drug Delivery

As noted above, the polymeric materials can be use as carriers for biologically active materials such as therapeutic, prophylactic or diagnostic agents, including hormones, enzymes, antibiotics, antineoplastic agents, and cell suspensions. The polymeric material may be used to temporarily preserve functional properties of an agent to be released, as well as provide prolonged, controlled release of the agent into local tissues or systemic circulation.

In a variation of the method for controlled drug deliver in which an agent is mixed with the macromer solution then polymerized in situ, the macromers are polymerized with the biologically active materials to form microspheres or nanoparticles containing the biologically active material. The macromer, photoinitiator, and agent to be encapsulated are mixed in an aqueous mixture. Particles of the mixture are formed using standard techniques, for example, by mixing in oil to form an emulsion, forming droplets in oil using a nozzle, or forming droplets in air using a nozzle. The suspension or droplets are irradiated with a light suitable for photopolymerization of the macromer.

These materials are particularly useful for controlled drug delivery of hydrophilic materials, since the water soluble regions of the polymer enable access of water to the materials entrapped within the polymer. Moreover, it is possible to polymerize the macromer composition containing the material to be entrapped without exposing the material to organic solvents. Release may occur by diffusion of the material from the polymer prior to degradation and/or by diffusion of the material from the polymer as it degrades, depending upon the characteristic pore sizes within the polymer, which is controlled by the molecular weight between crosslinks and the crosslink density. Deactivation of the entrapped material is reduced due to the immobilizing and protective effect of the gel and catastrophic burst effects associated with other controlled-release systems are avoided. When the entrapped material is an enzyme, the enzyme can be exposed to substrate while the enzyme is entrapped, provided the gel proportions are chosen to allow the substrate to permeate the gel. Degradation of the polymer facilitates eventual controlled release of free macromolecules in vivo by gradual hydrolysis of the terminal ester linkages.

III. Examples

As demonstrated by examples 1-3, three classes of NO-producing, PEG-based polymers have been synthesized and their NO release rate constants determined in vitro under physiological conditions. The biological response to appropriate materials has been evaluated in vitro using cultured smooth muscle cells and endothelial cells and in vivo using a rat carotid artery injury model that resembles restenosis in man. The materials include BAB block copolymers of polyethylene glycol (A) with polycysteine (B) that are subsequently reacted with $NaNO_2$ to form S-nitrosothiols, BAB block copolymers of polyethylene glycol ("PEG") (A) and diethylenetriamine ("DETA") (B) that are subsequently reacted with NO gas to form nucleophile/NO complexes, and BAB block copolymers of polyethylene glycol (A) and polylysine (B) that are subsequently reacted with NO gas to form nucleophile/NO complexes. All polymers are further terminated with reactive acrylate groups to allow rapid photopolymerization in situ.

Such materials would be expected to have good biocompatibility, provided that a water soluble, biocompatible polymer such as PEG comprises the bulk of the material and has a sufficiently high molecular weight, and to slowly biodegrade due to the presence of two ester bonds and two amide bonds in each polymer chain. These three materials were selected as they are expected to have vastly different release kinetics: nucleophile/NO complexes have been shown to release NO for up to 5 weeks (Smith et al., (1996) *J. Med. Chem.* 39:1148-56); while the half-life of S-nitrosocysteine is 0.023 hours (Mathews et al., (1993) *J. Pharmacol. Exp. Therap.* 267:1529-37). The amount of NO produced by these copolymers may be tailored by altering the ratio of polyethylene glycol (PEG) to cysteine or lysine.

An advantage of these macromer compositions are that they can be polymerized rapidly in an aqueous surrounding. Precisely conforming, semi-permeable, biodegradable films or membranes can thus be formed on tissue in situ to serve as biodegradable barriers, as carriers for living cells or other biologically active materials, and as surgical adhesives. The polymer shows excellent biocompatibility, as seen by a minimal fibrous overgrowth on implanted samples. Hydrogels for the models were gelled in situ from water-soluble precursors by brief exposure to long wavelength ultraviolet (LWUV) light, resulting in formation of an interpenetrating network of the hydrogel with the protein and glycosaminoglycan components of the tissue.

As demonstrated by examples 4 and 5, three types of PVA hydrogels were made and demonstrated release of NO and incorporated drug (bFGF): $PVA-NH_2-NO$ hydrogels; PVA-Cys-NO hydrogels; PVA-NO-bFGF hydrogels. The results are similar to those for the PEG based hydrogels.

Example 1

Synthesis of PEG-Cys-NO and Hydrogels Macromers

As shown in FIG. 1, an acryloyl-PEG-Cys-NO polymer was formed by first reacting polyethylene glycol N-hydroxysuccinimide monoacrylate (ACRL-PEG-NHS, MW 3400, commercially available from Shearwater Polymers, Huntington, Ala.) with L-cysteine at an 1:2 molar ratio in 50 mM sodium bicarbonate buffer (pH 8.5) for 2 hours; the product was then dialyzed in a cellulose ester membrane (Molecular weight cutoff 500, Spectrum Labs, Laguana Hills, Calif.) in $diH_2O$, and lyophilized. Analysis of the acryloyl-PEG-Cys copolymer was performed using gel permeation chromatography (GPC) with an evaporative light scattering detector and a UV detector at 260 nm (Polymer Laboratories, Amherst, Mass.). Successful synthesis of acryloyl-PEG-Cys was determined by a shift in the position of the peak from the evaporative light scattering detector. The copolymer was then reacted with an equimolar amount of $NaNO_2$ at pH 2 and 37° C. for 20 minutes to form S-nitrosocysteine. Conversion of thiol groups to S-nitrosothiols was measured using the Ellman's assay (Hermanson, (1995) *Bioconjugate Techniques*, San Diego, Calif. Academic Press; 88-90). After adjusting the pH of the solution to 7.4, the acryloyl-PEG-Cys-NO polymer was incorporated into photopolymerizable hydrogels by mixing with PEG-diacrylate (MW 3400) at a 1:10 molar ratio in aqueous solution with 1500 ppm 2,2-dimethoxy-2-phenyl acetophenone as a long wavelength ultraviolet initiator. 0.15% N-vinylpyrrolidone was present in this mixture as it was used as a solvent for the photoinitiator. Exposure to UV light (365 nm, 10 mW/cm$^2$) was used to crosslink the polymer, resulting in conversion to a hydrogel (Sawhney et al., (1993) *Macromol.* 26:581-7).

Example 2

Synthesis of PEG-Lys$_5$-NO-Macromer and Hydrogels

Figure 2:
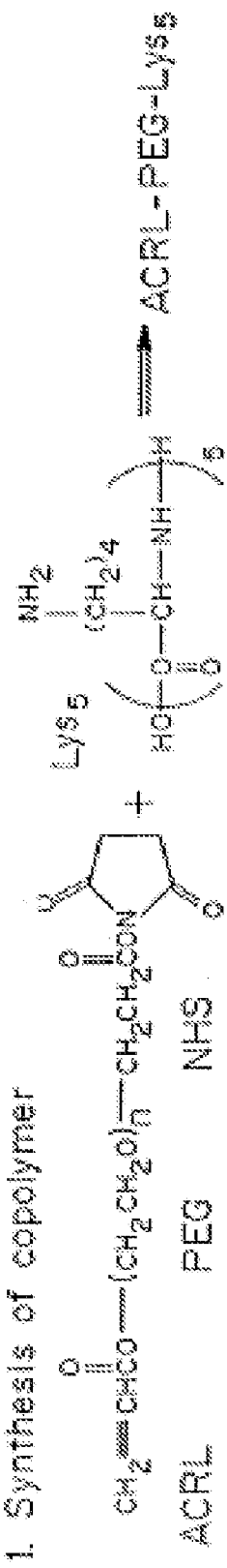
FIG. 2 is a schematic of the synthesis of acryloyl-PEG-Lysine$_5$ NO-nucleophile complex hydrogels.
Figure 2:
Figure 2:
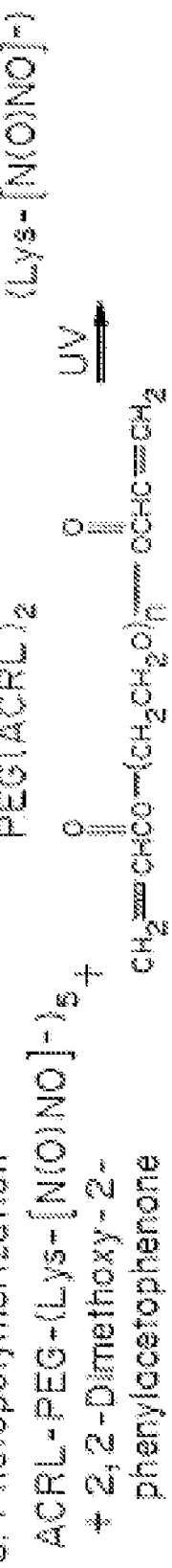
Figure 2:

As shown in FIG. 2, for acryloyl-PEG-Lys$_5$-NO hydrogels, a copolymer of ACRL-PEG-NHS (MW 3400, Shearwater Polymers) and poly-L-lysine (DP=5) was synthesized by reacting at an equimolar ratio in 50 mM sodium bicarbonate (pH 8.5). The resultant copolymer was analyzed via GPC, then dissolved in water and reacted with NO gas in an evacuated vessel, thus forming NO-nucleophile complexes with the amine groups on the lysine side groups. The extent of conversion of amine groups to NO-nucleophile complexes was measured using the ninhydrin assay, and crosslinked hydrogels were formed as described above in Example 1.

Example 3

Synthesis of PEG DETA-NO Macromers and Hydrogels

Figure 3:
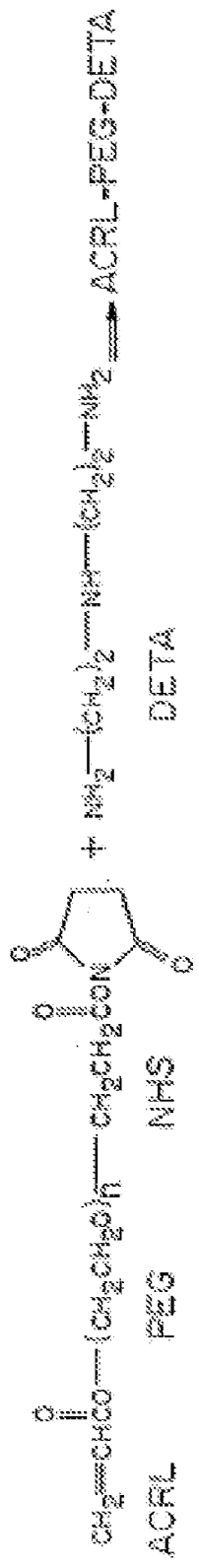
FIG. 3 is a schematic of the synthesis of acryloyl-PEG-DETA-NO-nucleophile complex hydrogels.
Figure 3:
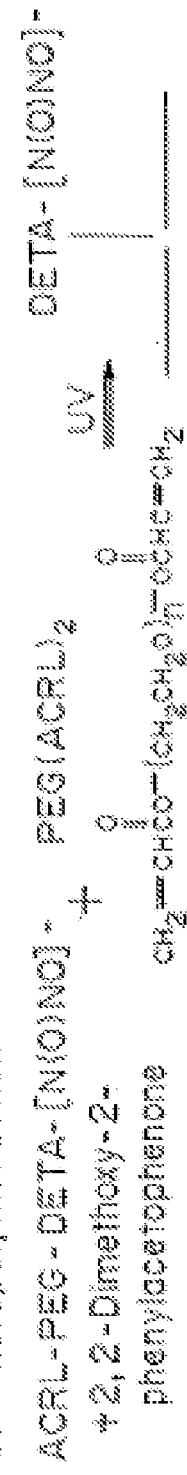
Figure 3:
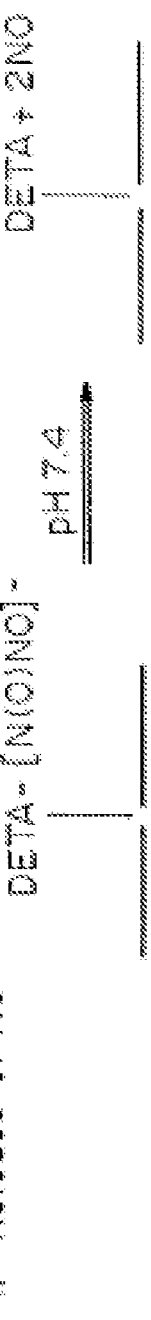

Diethylenetriamine (DETA, Aldrich, Milwaukee, Wis.) was reacted with ACRL-PEG-NHS (MW 3400, Shearwater Polymers) in 50 mM sodium bicarbonate buffer (pH 8.5) at an equimolar ratio, lyophilized, and analyzed via GPC as described above. The copolymer was then dissolved in water and exposed to NO gas to form NO-nucleophile complexes as described for PEG-Lys$_5$-NO and assayed for amine content using the ninhydrin assay. The PEG-DETA-NO was lyophilized and then photopolymerized as described above to form hydrogels, as shown in FIG. 3.

Example 4

Synthesis of PVA-NH$_2$-NO Macromers and Hydrogels

Poly(vinyl alcohol) (Hoechst, Mowiol 4-88) was dissolved in diH$_2$O and warmed to 95° C. in a round bottom flask under continuous stirring. After one hour, the solution was cooled to room temperature, and a crosslinkable acetal group, methacrylamidoacetaldehyde dimethyl acetal (NAAADA) was added. The amine acetal, gamma-aminobutyraldehyde diethyl acetal, was also added, and the mixture was acidified using glacial acetic acid and 37% hydrochloric acid. The mixture was allowed to stir at room temperature for nine hours, after which the pH was adjusted to pH 3.6 using triethylamine. In order to purify the polymer, the solution was then diafiltered through a MW 3000 cellulose membrane against diH$_2$O at 6.5 times the volume of polymer solution. The polymer concentration was adjusted to 22% w/v using diafiltration, and the pH was adjusted to 7.4 with 1N NaOH. The amine concentration of the polymer was determined using the ninhydrin assay.

In order to form the NO donor bound to the PVA-NH$_2$, the neutralized amine-modified polymer was placed in a round bottom flask with stopcock. The flask was evacuated and filled with nitric oxide gas until the desired conversion of amines to NO nucleophile complexes was achieved. Photocrosslinked hydrogels were formed from the PVA-NH$_2$-NO by adding 0.1% IRGACURE+198 2959 (Ciba-Geigy) photoinitiator (based on total solution volume) and then exposing to UV light (2 mW/cm$^2$, 365 nm) for 30 seconds. Addition of the photoinitiator brings the final polymer concentration to 20% w/v.

Example 5

Synthesis of PVA-Cys-NO Macramers and Hydrogels

PVA-NH$_2$ was synthesized as described above. The amine terminus of cysteine was acetylated using acetic anhydride, and the carboxyl end of the cysteine was coupled to the PVA-NH$_2$ using water-soluble EDAC chemistry. The resulting PVA-Cys was then purified using diafiltration and brought to a concentration of 22% w/v. PVA-Cys-NO was formed by adding sodium nitrite at an equimolar amount to cysteine residues, adjusting to pH to 2, and incubating at 37° C. for 15 minutes. The extent of reaction of cysteine to Cys-NO was assayed using both the Ellman's and Griess reactions. The photoinitiator, 2,2-methyl-2-phenylacetophenone was dissolved in N-vinylpyrrolidone at a concentration of 600 mg/ml and added to the polymer solution (0.1% based on total solution volume). The polymer was then crosslinked under UV light for 30 seconds and placed in HEPES buffered saline, pH 7.4, 37° C.

Example 6

Synthesis of PVA-NO-bFGF Hydrogels

For PVA-NO-bFGF hydrogels, the above procedure was used to make the PVA-NO polymer. Immediately prior to exposure to UV light, 25 µg/ml bFGF was added to the polymer solution and mixed well. Gels were crosslinked as described earlier and stored in HEPES buffered saline, pH 7.4, 37° C.

Example 7

NO Release from Hydrogels

Following preparation and photopolymerization of the NO-releasing materials as described above, the hydrogels were weighed and stored in HEPES buffered saline, pH 7.4, at 37° C. Aliquots of the buffer were removed at each time point and replaced with fresh buffer. The samples from each time point were then analyzed for nitrite content using a colorimetric assay based on the Griess reaction.

NO release kinetics of hydrogels stored in buffer at various pH levels were also investigated in order to explore possible storage conditions for the hydrogels. At acidic pH levels, release of NO from the hydrogels was significantly inhibited.

Figure 4:
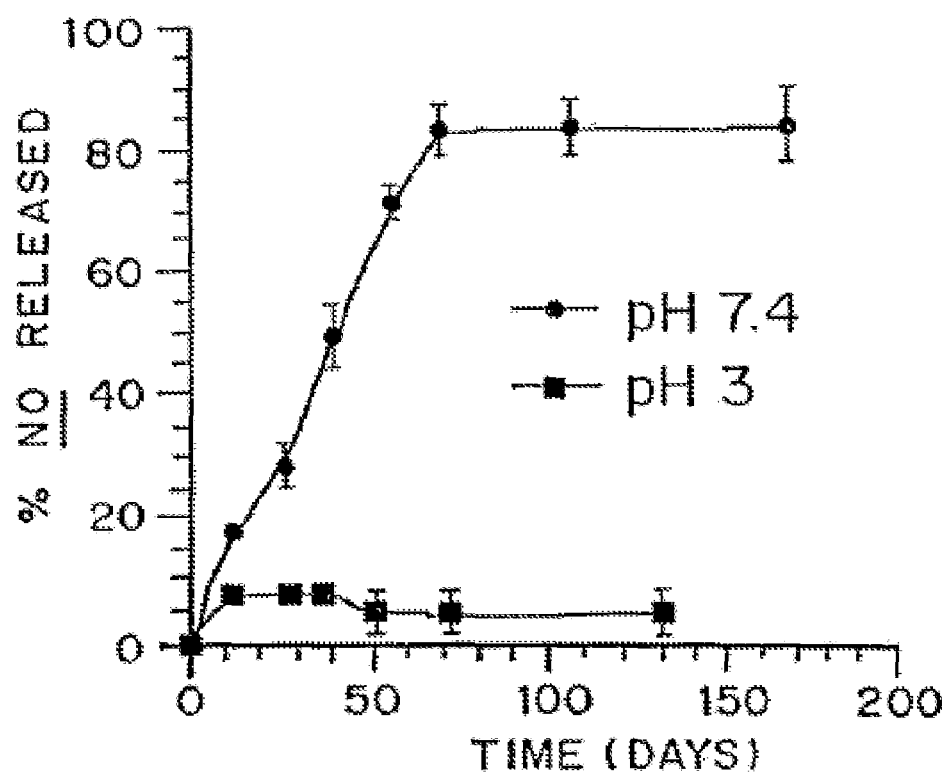
FIG. 4 is a graph showing the temporal release (% NO released over time in days) of NO from acryloyl-PEG-Lys$_5$-NO hydrogels at pH 7.4 (circles) and pH 3 (squares).

NO release from acryloyl-PEG-Lys$_5$-NO hydrogels is shown in FIG. 4.

Figure 5:
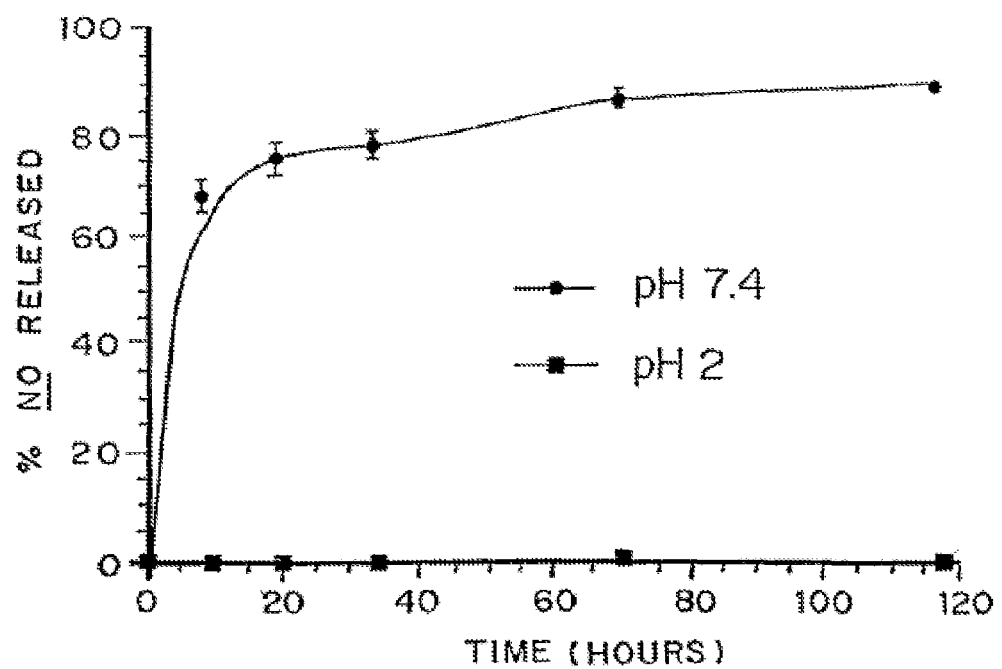
FIG. 5 is a graph showing the temporal release (% NO released over time in hours) of NO from acryloyl-PEG-DETA-NO hydrogels at pH 7.4 (circles) and pH 2 (squares).

NO release from acryloyl-PEG-DETA-NO hydrogels is shown in FIG. 5.

Figure 6:
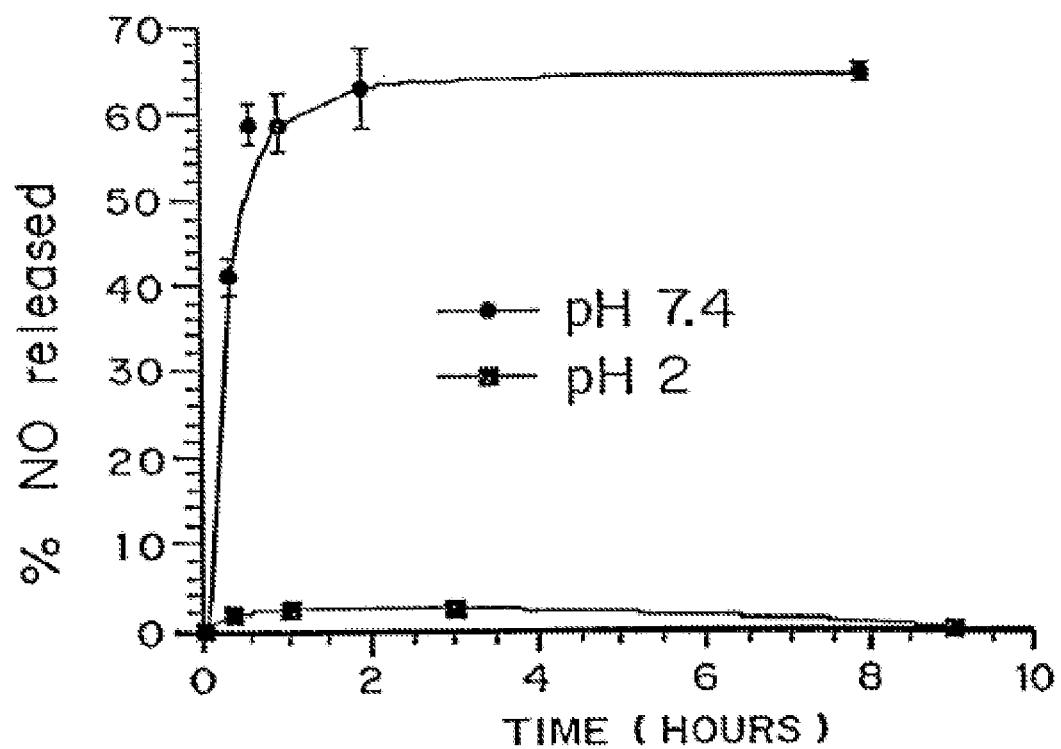
FIG. 6 is a graph showing the temporal release (% NO released over time in hours) of NO from PEG-Cys-NO hydrogels at pH 7.4 (circles) and pH 2 (squares).

NO release from acryloyl-PEG-Cys-NO hydrogels is shown in FIG. 6.

Example 8

NO and bFGF Release from PVA-NO-bFGF Hydrogels

Figure 7A:
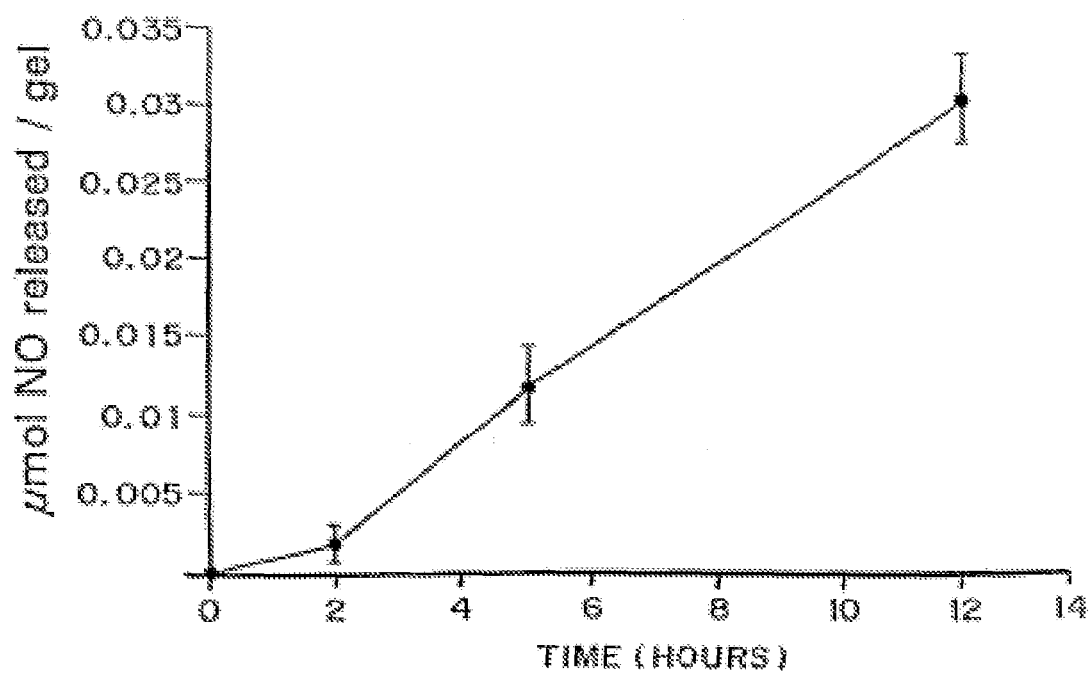
FIG. 7A is a graph showing the temporal release (μmol NO released per gram of polymer over time in hours) of NO from PVA-NO-bFGF hydrogels at pH 7.4, 37° C.
Figure 7B:
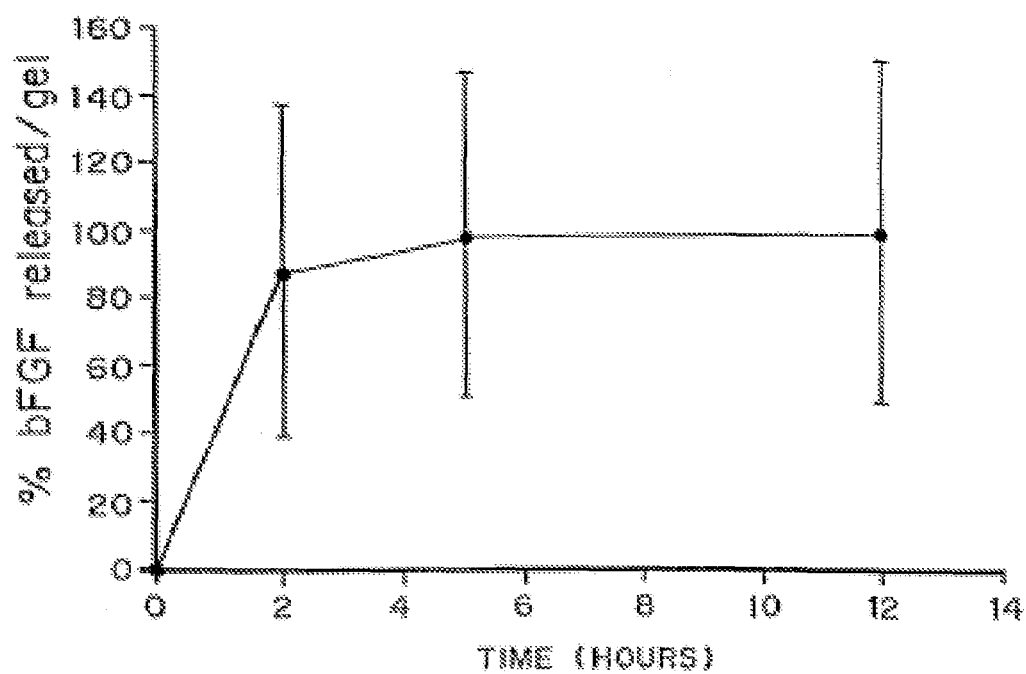
FIG. 7B is a graph showing the temporal release (% of theoretical bFGF released peer gram of gel over time in hours) from PVA-NO-bFGF hydrogels at pH 7.4, 37° C.

The release of NO release from PVA-NO-bFGF hydrogels prepared as described in Example 6 was determined in the same manner as Example 7 and is shown in FIG. 7A. Release of bFGF was quantified using that BCA assay (Pierce Chemicals) and is shown in FIG. 7B. Release of NO continues for well over 12 hours, while the growth factor is completely released within the first 5 hours.

Example 9

Effects of NO-releasing Macromers on Cultured Smooth Muscle Cells: Proliferation and Viability In order to assess the potential of a material for the reduction of smooth muscle cell proliferation after vascular injury, cultured smooth muscle cells were grown in the presence of NO-releasing materials, and the effects of those materials on the cells evaluated. Smooth muscle cells isolated from Wistar-Kyoto rats (passage 11-15, provided by T. Scott-Burden) were cultured in Minimum Essential Medium supplemented with 10% FBS, 2 mM L-glutamine, 500 units penicillin, and 100 mg/L streptomycin, at 37° C. in a 5% CO$_2$ environment. The cells were seeded into 24-well tissue culture plates (Becton Dickinson, Franklin Lakes, N.J.) at a density of 10,000 cells/cm$^2$. NO donors in either soluble or hydrogel form were added to the media in the wells one day after seeding. At 4 days culture, cell numbers were determined by preparing single cells suspensions with trypsin and counting three samples from each group using a Coulter counter (Multisizer #0646, Coulter Electronics, Hialeah, Fla.).

The effects of No donors in solution on the proliferation of SMCs were first investigated by performing a NO dose response curve, whereupon cells were cultured with a range of NO donor concentrations (1 μM-10 mM) in order to identify appropriate dosages for hydrogel studies. NO-nucleophile complexes (Lys-NO and DETA-NO) were formed by reacting either L-lysine or DETA with NO gas in water for 24 hours. Soluble Cys-NO was synthesized by reacting an equimolar amount of L-cysteine with $NaNO_2$ at pH 2 and 37° C. for 20 minutes. All NO donor solutions were adjusted to pH 7.4 prior to addition to cell cultures.

Smooth muscle cell proliferation in the presence of NO-producing and control hydrogels was then investigated using the optimal NO dose determined above. Hydrogels containing acryloyl-PEG-Lys-NO, PEG-DETA-NO, and acroyl-PEG-$Lys_5$NO, were formed as described above, except that the gel solutions were sterile filtered through 0.2 μm syringe filters (Gelman Sciences, Ann Arbor, Mich.) prior to adding 2,2-dimethoxy-2-phenyl acetophenone. PEG-diacrylate hydrogels containing no NO donors were used as a control. The hydrogels were photopolymerized in cell culture inserts (8 μm pore size, Becton Dickinson, Franklin Lakes, N.J.) and placed in the media over the cultured cells.

All three hydrogel No donors significantly inhibited SMC growth ($p<0.0001$). The number of smooth muscle cells remained near that of the seeding density, which ranged from 10-15% of the final control cell number for all experiments.

Figure 8A:
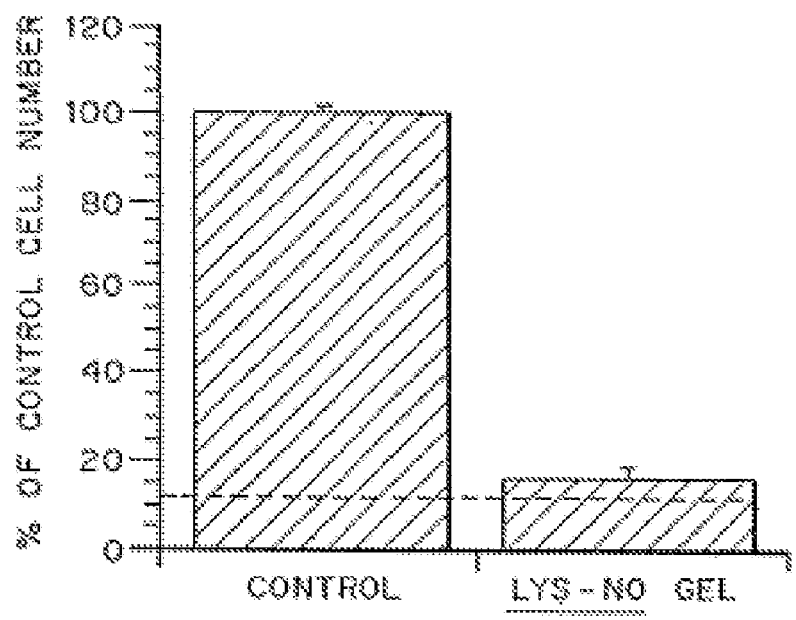
FIGS. 8A and 8B are graphs showing that acryloyl-PEG-Lysine-NO hydrogels inhibit the proliferation of smooth muscle cells.
Figure 8B:
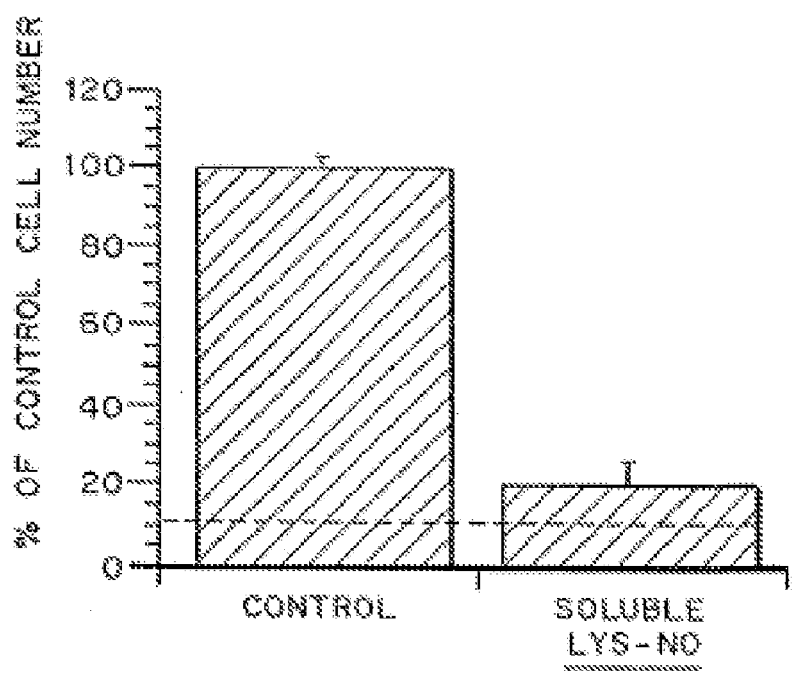

Inhibition of SMC proliferation by acryloyl-PEG-$Lys_5$-NO hydrogels is shown in FIG. 8A, compared to the macromer solution control shown in FIG. 8B. Both significantly inhibited SMC proliferation.

Figure 9A:
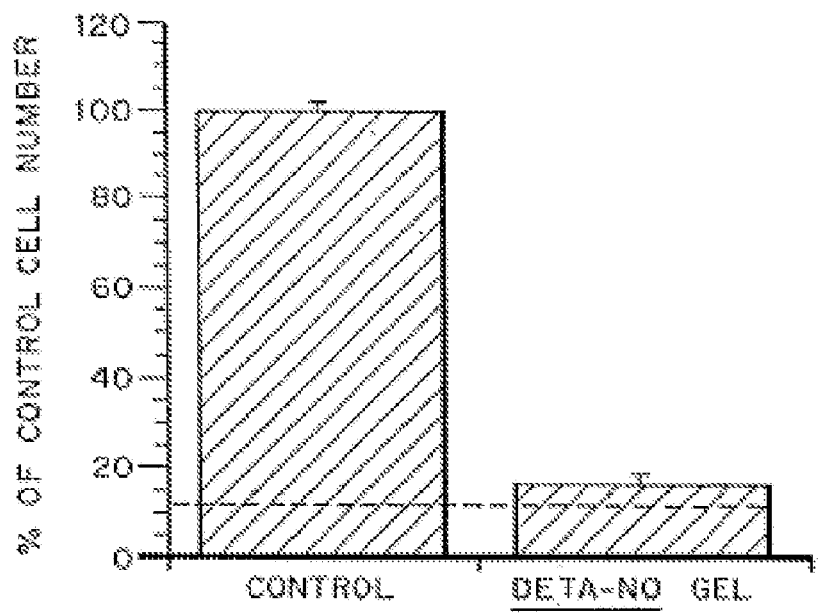
FIGS. 9A and 9B are graphs showing the inhibition of SMC proliferation by NO released from acryloyl-PEG-DETA-NO hydrogels (FIG. 9A) and soluble polymer (FIG. 9B), as a percentage of the control.
Figure 9B:
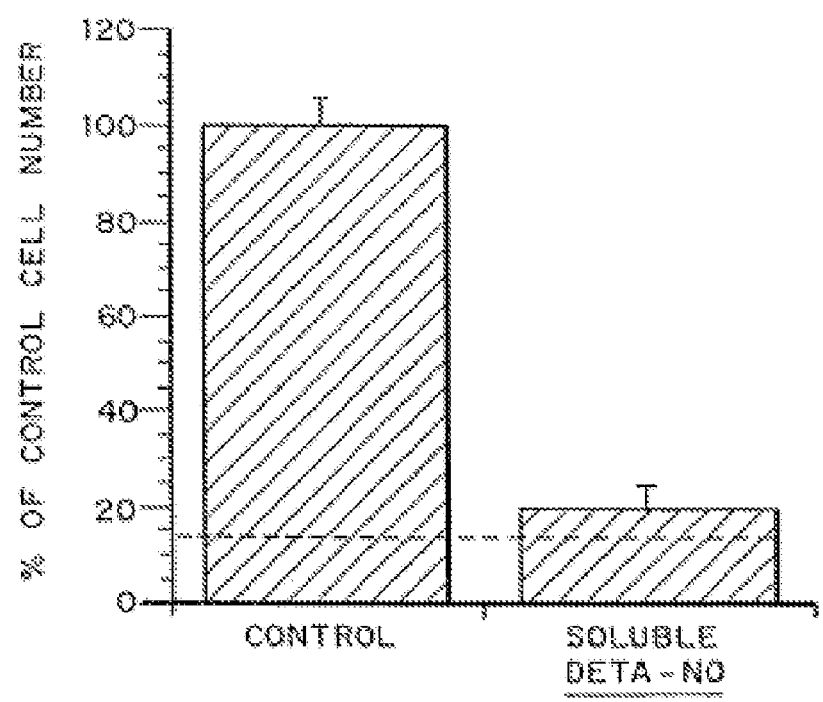

Inhibition of SMC proliferation by acryloyl-PEG-DETA-NO-nucleophile complex hydrogels is shown in FIG. 9A, compared to the macromer solution control shown in FIG. 9B. Both significantly inhibited SMC proliferation.

Figure 10A:
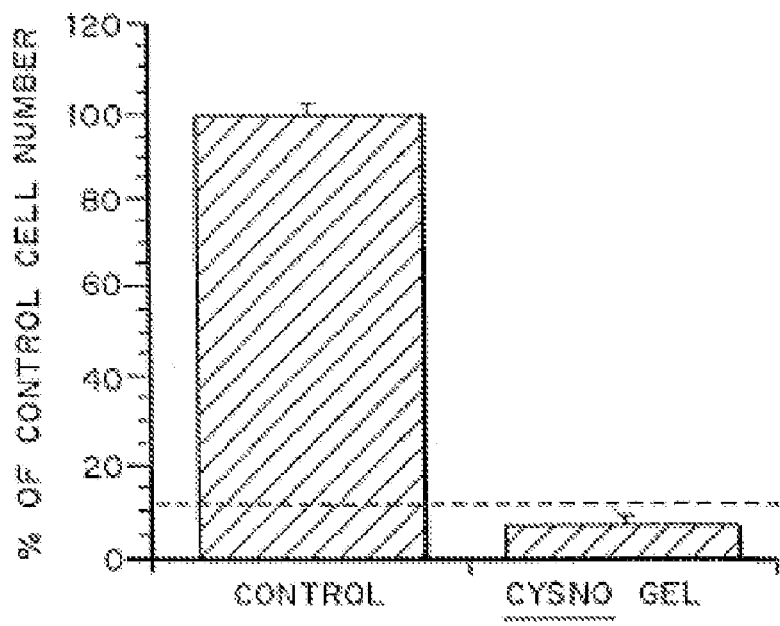
FIGS. 10A and 10B are graphs showing inhibition of SMC proliferation by NO released from acryloyl-PEG-Cys-NO hydrogels (FIG. 10A) and soluble polymer (FIG. 10B), as a percentage of controls.
Figure 10B:
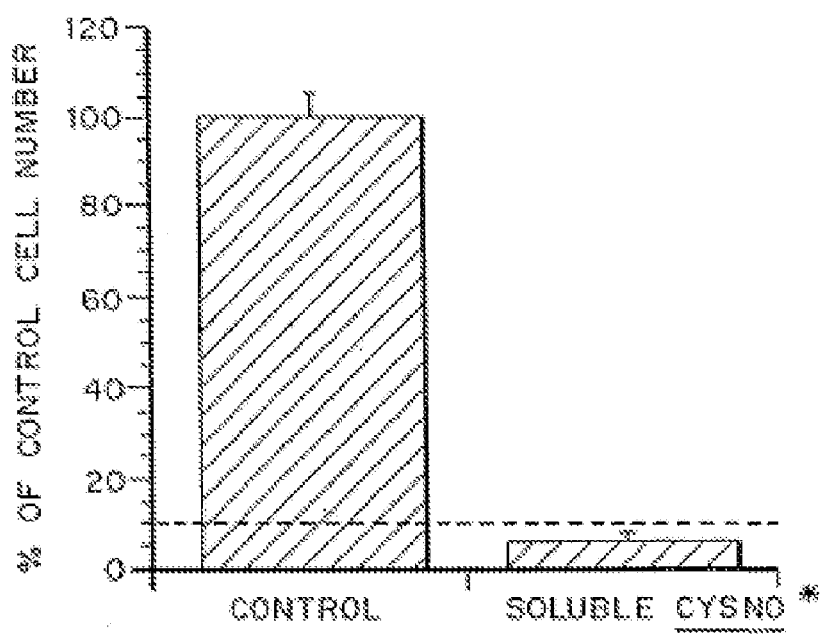

Inhibition of SMC proliferation by acryloyl-PEG-Cys-NO hydrogels is shown in FIG. 10A, compared to the macromer solution control shown in FIG. 10B. Both significantly inhibited SMC proliferation.

Figure 11:
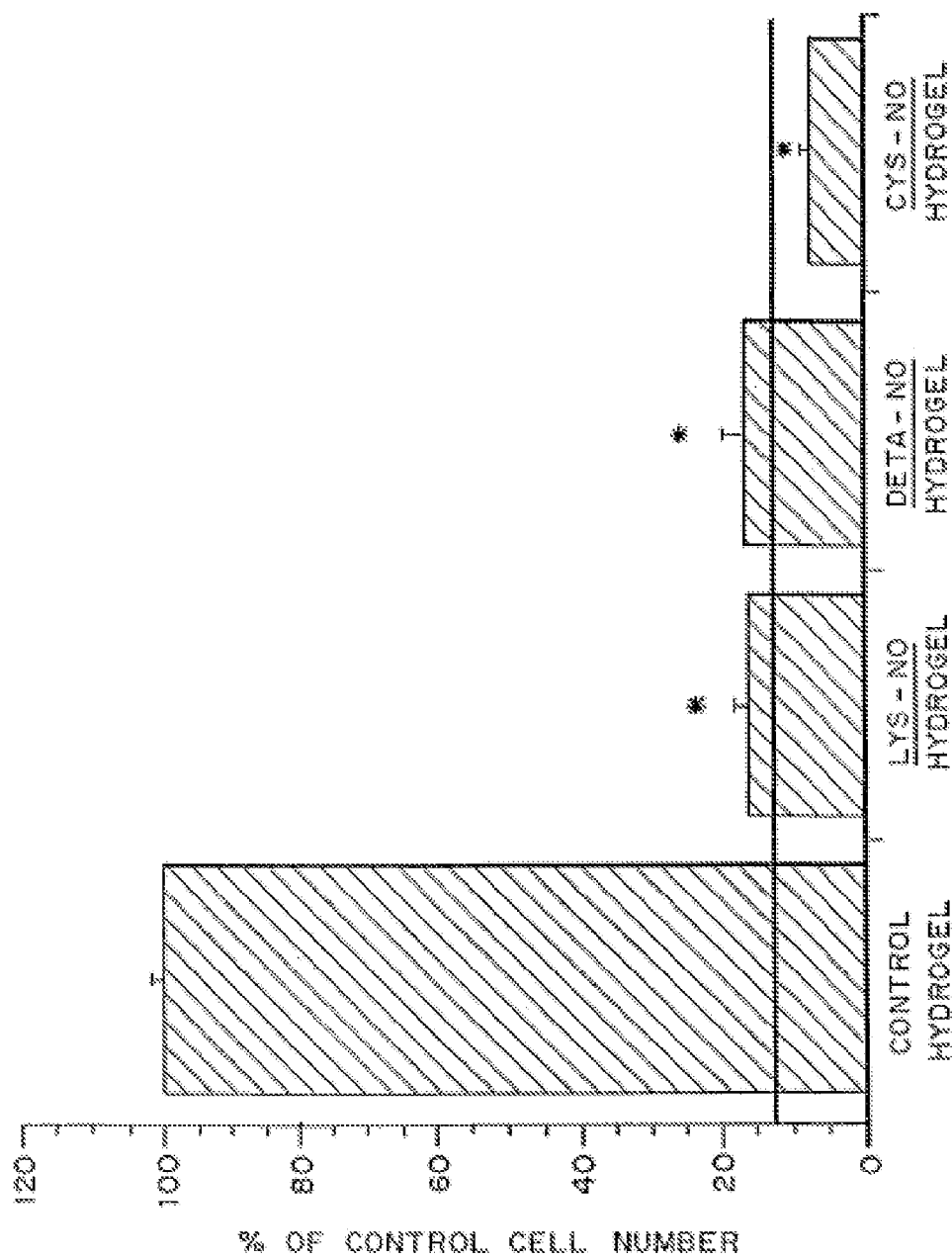
FIG. 11 is a graph comparing the degree of inhibition of smooth muscle cell growth by NO released from hydrogels: acryloyl-PEG-Lys-NO, acryloyl-PEG-DETA-NO, and acryloyl-PEG-Cys-NO, compared to control hydrogel with NO. The percent inhibition of smooth muscle cell growth is determined by comparing the cell growth for each NO-releasing hydrogel to a control PEG-diacrylate hydrogel.

Inhibition of SMC proliferation by acryloyl-PEG-Cys-NO hydrogels, acryloyl-PEG-DETA-NO hydrogels, and acryloyl-PEG-Lys-NO hydrogels is compared to the control hydrogel in FIG. 11. All of the NO hydrogels significantly inhibited SMC growth.

Example 10

Effects of NO-releasing Macromers on Platelet Adhesion in vitro

The effect of No release on platelet adhesion was investigated to assess the potential of these materials for prevention of thrombosis. Blood was obtained from a healthy volunteer by venipuncture and anticoagulated with 10 U/ml heparin. Platelets and white blood cells were fluorescently labeled with mepacrine at a concentration of 10 μM. A solution of 2.5 mg/ml collagen I in 3% glacial acetic acid in $diH_2O$ was prepared and applied to glass slides for 45 minutes in a humidified environment at room temperature. Acryloyl-PEG-Cys-NO and PEG-diacrylate hydrogels were prepared as described above and incubated with the labeled whole blood at 37° C. for 30 minutes. The hydrogels were removed and the blood was then incubated with the collagen-coated glass slides (two per group) for 20 minutes at 37° C. and then rinsed with HBS. Platelet counts per field of view at 40× were counted under a fluorescent microscope (Zeiss Axiovert 135, Thornwood, N.Y.) in four randomly chosen areas per slide.

Photos of platelets which had been exposed to control PEG-diacrylate or acryloyl-PEG-Cys-NO hydrogels demonstrate that exposure to the NO-releasing hydrogels inhibits platelet adhesion to thrombogenic surface. Glass slides coated with collagen were used as a thrombogenic surface to which platelets would normally adhere. When the blood was incubated with control PEG-diacrylate hydrogels, 69.25±4.46 (mean±SD) adherent platelets were observed per field of view. This number was reduced to 7.65±6.16 platelets pre field of view when blood was pre-exposed to the acryloyl-PEG-Cys-NO hydrogels ($p<0.0001$).

Modifications and variations of the methods and materials described herein will be obvious to those skilled in the art from the foregoing detailed description and accompanying figures. These methods and materials are intended to be encompassed by the following claims.

We claim:

1. A method for controlled release of NO or an NO donor comprising administering to tissue a biocompatible, polymerizable, macromer composition comprising at least one NO carrying region or the NO donor, wherein NO or the NO donor is complexed to the macromer composition, and wherein the NO or the NO donor is released from the macromer composition following polymerization in situ, under physiological conditions, wherein the macromer composition comprises one or more region selected from the group consisting of water soluble regions, tissue adhesive regions, and polymerizable end group regions and one or more therapeutic or diagnostic agents selected from the group consisting of proteins, carbohydrates, nucleic acids, organic molecules, inorganic molecules, biologically active molecules, cells, tissue, and tissue aggregates.

2. The method of claim 1 wherein the macromer composition is water soluble.

3. The method of claim 1, wherein the macromer comprises a water soluble region, an NO carrying region, a cell adhesion ligand, and a free radical polymerizable region.

4. The method of claim 1, wherein the water soluble region is polyvinyl alcohol and the polymerizable group is an acrylamide.

5. The method of claim 1, wherein the macromer composition comprises an acryloyl-PEG-Cys-NO macromer.

6. The method of claim 1, wherein the macromer composition comprises an acryloyl-PEG-$Lys_5$-NO macromer.

7. The method of claim 1, wherein the macromer composition comprises a PEG-DETA-NO macromer.

8.

9. The method of claim 1, wherein the macromer composition comprises a PVA-Cys-NO macromer.

10. The method of claim 1, wherein the macromer composition comprises a PVA-NO-βFGF macromer.

11. The method of claim 1, wherein the macromer composition is administered to a smooth muscle cell tissue.

12. The method of claim 1, wherein the macromer composition is administered to blood.

13. The method of claim 1, wherein the macromer composition further comprises at least one degradable region.

14. The method of claim 13, wherein the degradable region is attached to a water soluble region, and a polymerizable end group region is attached to the degradable region.

15. The method of claim 13, wherein a water soluble region is attached to the degradable region, and the polymerizable end group region is attached to the water soluble region.

16. The method of claim 1, further comprising initiating polymerization in situ.

17. A method of reducing formation of surgical adhesions comprising administering to an individual in need thereof a biocompatible, polymerizable, macromer composition comprising at least one NO carrying region or an NO donor, wherein NO or the NO donor is complexed to the macromer composition, and wherein the NO or the NO donor is released from the macromer composition following polymerization in situ, under physiological conditions, wherein the macromer composition comprises regions selected from the group consisting of water soluble regions, tissue adhesive regions, and polymerizable end group regions.

18. The method of claim 17 wherein the macromer further comprises degradable regions.

\* \* \* \* \*